(12) United States Patent
Lihl et al.

(10) Patent No.: US 8,516,909 B2
(45) Date of Patent: Aug. 27, 2013

(54) CRYOPREPARATION CHAMBER FOR MANIPULATING A SAMPLE FOR ELECTRON MICROSCOPY

(75) Inventors: Reinhard Lihl, Vienna (AT); Michael Zimmermann, Leopoldsdorf (AT)

(73) Assignee: Leica Mikrosysteme GmbH, Vienna (AT)

( * ) Notice: Subject to any disclaimer, the term of this patent is extended or adjusted under 35 U.S.C. 154(b) by 448 days.

(21) Appl. No.: 12/841,240

(22) Filed: Jul. 22, 2010

(65) Prior Publication Data

US 2011/0027876 A1    Feb. 3, 2011

(30) Foreign Application Priority Data

Jul. 29, 2009   (AT) .................................. 1187/2009

(51) Int. Cl.
*G01N 1/42*     (2006.01)
(52) U.S. Cl.
USPC ........................................................ 73/863.11
(58) Field of Classification Search
USPC ........................................................ 73/863.11
See application file for complete search history.

(56) References Cited

U.S. PATENT DOCUMENTS

| | | | | |
|---|---|---|---|---|
| 5,044,165 A | * | 9/1991 | Linner et al. | 62/55.5 |
| 5,832,584 A | * | 11/1998 | Folino et al. | 29/407.04 |
| 7,816,141 B2 | * | 10/2010 | Bose | 436/5 |
| 2004/0157284 A1 | | 8/2004 | Frederik et al. | |

FOREIGN PATENT DOCUMENTS

| | | |
|---|---|---|
| EP | 1370846 B1 | 6/2007 |
| WO | 02/077612 A1 | 10/2002 |

* cited by examiner

*Primary Examiner* — Hezron E Williams
*Assistant Examiner* — Paul West
(74) *Attorney, Agent, or Firm* — Hodgson Russ LLP

(57) ABSTRACT

The present invention relates to a cryopreparation chamber (100) for preparing and manipulating a sample for electron microscopy, the cryopreparation chamber (100) being cooled by a primary cryogen, the cryopreparation chamber (100) including a first and a second chamber portion (101,102), the second chamber portion (102) being detachably placeable (101) on the first chamber portion (101), and moreover, the second chamber portion (102) being provided, in its outer wall (106), with an access port (107) through which a specimen holder (108) for an electron microscope can be inserted into the cryopreparation chamber (100). The present invention also relates to a cryopreparation device (200) which is suitable for cryopreparing a sample for an electron microscope and includes such a cryopreparation chamber (100).

20 Claims, 6 Drawing Sheets

CRYOPREPARATION CHAMBER FOR MANIPULATING A SAMPLE FOR ELECTRON MICROSCOPY

CROSS REFERENCE TO RELATED APPLICATIONS

This application claims priority of the Austrian patent application number 1187/2009 filed Jul. 29, 2009, the entire disclosure of which is incorporated by reference herein.

FIELD OF THE INVENTION

The present invention relates to a cryopreparation chamber for preparing and manipulating a sample for electron microscopy, the cryopreparation chamber being cooled by a first (primary) cryogen.

BACKGROUND OF THE INVENTION

Cryo-electron microscopy has turned out to be particularly suitable for analysis of biological structures. In this technology, a hydrous sample is cryofixed; i.e., it is cooled very rapidly, avoiding the formation of ice crystals. The objects to be examined, such as cells, enzymes, viruses or lipid layers, are thereby embedded in a thin vitrified ice layer. The great advantage of cryofixation is that the biological structures are maintained in their native state and can be examined in their physiological environment. Among other things, cryofixation allows a biological process to be arrested at any desired time and to be examined in this vitrified state in the cryo-electron microscope.

Regardless of the type of sample preparation, transmission electron microscopic imaging requires that the sample be sufficiently thin. Samples used for the transmission electron microscope typically have a thickness of 30-100 nm, preferably of 50-80 nm. When using other transmission electron microscopic methods (e.g., intermediate voltage transmission electron microscopy (IVEM)), the samples may be significantly thicker. Samples of defined thickness can be obtained by sectioning using an ultramicrotome. In the process, a cryofixed sample is cut into very thin slices (cryosections). Another preparation method is to deposit thin liquid films on electron microscopic supports. In this method, a thin liquid film is frozen very rapidly, avoiding the formation of ice crystals. To this end, an electron microscopic support ("grid") is immersed in a sample-containing liquid or, alternatively, the sample liquid is pipetted onto the support, excess liquid is removed, for example, using a filter paper, and the liquid film remaining on the support is cryofixed by plunging it into a bath of liquid ethane, for example. Cryofixed samples can be examined directly in the frozen state in a cryo-electron microscope, since they are able to withstand the high vacuum present in the electron microscope.

Automated and semi-automated cryopreparation devices used for cryofixation are known in the art. International Patent Application WO 02/077612 A1 (see also EP 1 370 846 B1 and US 020040157284) discloses such a device, which allows cryopreparation to be performed in a substantially automated manner. This device is marketed under the trade name Vitrobot™. In this device, the sample support is fixed in a holding device. Excess sample liquid is removed, if necessary, using a filter paper (blotting). Then, the support is rapidly plunged into a cryogenic bath (ethane), causing the sample to vitrify. Another device is produced by the Gatan Company (www-.gatan.at) under the trade name Cryoplunge™. This device is simpler in construction and not fully automated.

In the known devices, the cryogen used for cryofixing the sample is located in a cryopreparation chamber which is open at the top (e.g., the liquid nitrogen workstation of the Gatan Cryoplunge™ device). Cooling of the cryogen is accomplished using an additional cryogen, typically liquid nitrogen. Further, the cryopreparation chamber is cooled by a stream of cold gas produced by evaporation of the liquid nitrogen.

After the cooling process, the sample support carrying the vitrified sample is transferred in several steps from the ethane into a cooled specimen holder for an electron microscope. This transfer of the cryofixed sample is very critical because contact with moist air causes the immediate formation of a layer of ice crystals on the sample. According to the common procedure, the sample support carrying the frozen sample is removed from the ethane and initially transferred into a transfer box (e.g., a grid box). This step is carried out in the above-mentioned cryopreparation chamber filled with cold nitrogen gas. The transfer box is in turn introduced into a metal container, which is typically cooled with liquid nitrogen. This metal container is then transferred into a loading station for a cooled specimen holder for an electron microscope, the mounting of the sample support in the cooled specimen holder being performed in the loading station. Both the insertion of the sample support into the transfer box, and the transfer of the transfer box into the loading station for the cooled specimen holder for an electron microscope (EM), are critical procedures and involve a potential for contamination.

SUMMARY OF THE INVENTION

It is, therefore, an object of the present invention to enable a cryofixed sample located in a cryogenic bath to be transferred from the cryogenic bath into a cooled specimen holder for an electron microscope with minimum sample contamination.

This object is achieved by a cryopreparation chamber of the type mentioned at the outset, which in accordance with the present invention, includes a first and a second chamber portion, the second chamber portion being detachably placeable on the first chamber portion, and moreover, the second chamber portion being provided, in its outer wall, with an access port through which a specimen holder for an electron microscope can be inserted into the cryopreparation chamber.

Thanks to the invention, the sample support carrying the cryofixed sample can be removed from the cryogenic bath and mounted in the cooled specimen holder for an electron microscope directly within the cryopreparation chamber without any intermediate transfer. The above-described critical and cumbersome transfer steps of the conventional procedure are eliminated, allowing the risk of contamination to be minimized. The present invention not only provides advantages with respect to ensuring sample quality, but also for the user. On the one hand, the transfer of the sample is more convenient and easier to handle for the user. On the other hand, manipulation errors and safety hazards involved in handling liquid cryogen can be reduced.

The term "chamber portion" will be understood to refer to the housings constituting the first and second chamber portions as well as the interiors thereof.

The access port is adapted particularly for specimen holders for electron microscopy (hereinafter referred to as "EM specimen holders") that are lancet-shaped.

The EM specimen holders mainly used are side-entry goniometers. For this reason, the access port of the second chamber portion is adapted particularly for insertion of a side-entry goniometer.

Conveniently, the access port is arranged laterally in the outer wall of the second chamber portion. In a first advantageous variant, the EM specimen holder is inserted substantially horizontally into the second chamber portion. A substantially horizontal orientation of the EM specimen holder allows the sample support carrying the frozen sample to be easily mounted in the EM specimen holder.

In another variant, the EM specimen holder is inserted in an obliquely downward direction. In this manner, and because of the thermal stratification typically present in the cryopreparation chamber, the mounting process of the sample support may be displaced to a colder zone.

The dimensions of the access port are always adapted to the particular EM specimen holder employed, the design of which varies depending on the type or manufacturer. Since the second chamber portion having the access port is designed to be placeable on the first chamber portion, the access port may be changed very easily.

For most applications, it is sufficient if the second chamber portion has exactly one access port. However, for special applications, the present invention does not preclude the option of providing more than one access port in the outer wall of the second chamber portion.

As in the single-piece cryopreparation chambers known from the prior art, a first cryogen is used for cooling the cryopreparation chamber of the present invention. The term "primary cryogen" as also used herein refers to the cryogen for cooling the interior of the cryopreparation chamber and is preferably liquid nitrogen. To this end, in a preferred variant, the first chamber portion of the cryopreparation chamber of the present invention has a cooling bath for the primary cryogen. Evaporation of the liquid nitrogen produces a stream of cold gas which flows continuously upward, cooling the cryopreparation chamber and keeping it substantially free of ice precipitates. For purposes of cryofixation of electron microscopic samples, the first chamber portion further has a cooling bath for a second cryogen. The term "secondary cryogen" as also used herein refers to the cryogen used for vitrifying the sample and is preferably ethane. The sample support carrying the sample thereon is rapidly plunged into the cooling bath containing the secondary cryogen.

In order for the secondary cryogen to be cooled by the primary cryogen, it is convenient if at least a lower portion of the cooling bath for the second cryogen is disposed in the cooling bath for the primary cryogen. Further, the wall of the cooling bath for the second cryogen may have a heater for bringing the secondary cryogen to a desired temperature. In the case of ethane, the ethane is brought to a temperature at which it is in the liquid state and which is preferably −170° C.

The term "sample support" refers to all supports that are suitable for electron microscopy and electron microscopic sample preparation. In particular, the term "sample support" refers to the grids ("support grids") mentioned earlier above. The grids may have holes of different shape (honeycombs, slots, etc.) or a mesh having a defined mesh number and/or be coated with a film (e.g., coated grids of the Quantifoil Company) and/or be coated with vapor-deposited carbon. Another type of grid (referred to as "grid with tab", "tabbed grid", or "handle grid") has, in addition, a tab at the outer edge. This tab is located outside the normal radius of the grid and can be gripped with a forceps.

In a preferred variant, the second chamber portion is placed on the first chamber portion only after cryofixation of the sample. In automated cryopreparation devices, the sample support is clamped in a vertically mounted holding device, which is in turn disposed in a chamber which can be climate-controlled. The climate-controlled chamber is located immediately above the first chamber portion of the cryopreparation chamber. This approach has the great advantage that the distance between the climate-controlled chamber and the cryogenic bath containing the secondary cryogen can be kept very short during the plunging of the sample support with the sample into the secondary cryogen. A longer distance, which would result if the second chamber portion were in its mounted position, would have a negative effect on the sample during the plunging of the sample support into the secondary cryogen, because the sample support would travel a longer distance through the cold gas (nitrogen) which has a lower cooling effect and a potential for the formation of ice crystals.

After the freezing process, the climate-controlled chamber is raised, for example, by a stepper motor, and it is only then that the second chamber portion is placed on the first chamber portion.

Although the aforedescribed procedure is preferred because of the above-mentioned advantage of the short distance between the climate-controlled chamber and the cryogenic bath for the second cryogen, it is not precluded that the second chamber portion could be placed on the first chamber portion prior to the freezing process.

In a variant, the second chamber portion may be formed as one piece and be placed on the first chamber portion from above.

In most cases, however, the second chamber portion is placed on the first chamber portion only after the sample is plunged into the cryogen for cryofixation, as described above. During this process, the sample support is still fixed in the holding device which, in an automated cryopreparation device, is arranged in a vertical orientation. Therefore, it is generally not possible for the second chamber portion to be placed on the first chamber portion from above. In order for the holding device carrying the sample to be enclosed by the second chamber portion, it is advantageous that the device forming the second chamber portion be divided into at least two components which are reversibly placeable on the first chamber portion in a sideways direction, the access port being provided in one of the at least two components. In a sub-variant, the second chamber portion may first be closed around the holding device in a sideways direction slightly above the first chamber portion, and then be vertically placed on the first chamber portion. Further, the second chamber portion may be securable to the first chamber portion, for example using a bayonet connection of known type. The components may be joined and separated by known releasable connections such as, for example, a magnetic connection or a snap-fit connection.

In order to make the reversible sideways placement of the second chamber portion as easy and comfortable as possible, it is advantageous that the at least two components be pivotably connected to each other, for example, by a hinge. In this manner, the second chamber portion can be easily opened and closed.

In a sub-variant, the hinge may be designed such that the component provided with the access port for an EM specimen holder can be easily replaced by a component that has an access port for a different EM specimen holder (e.g., one having a different diameter).

In a variant that is particularly easy to use, the second chamber portion is composed of exactly two components. Preferably, each of the components constitutes one half of the second chamber portion.

Advantageously, the main body of the second chamber has substantially the shape of a cylindrical tube. Because of this, the second chamber portion can be placed on the first chamber portion with ease and without jamming.

For reasons of contamination, and for the temperature of the secondary cryogen used for cryofixation, it is advantages that the region of cold gas above the cryogen container in the first chamber portion be higher when the second chamber portion is not placed on the first chamber portion. This prevents airborne moisture from dissolving in the secondary cryogen, and unwanted ice crystals from forming on the sample. However, the higher region of cold gas above the cryogen container would have a negative effect on the sample during the plunging of the sample support into the cryogen, because the sample support would travel a longer distance through the cold gas (lower cooling effect, formation of ice crystals). This problem can be solved by a sleeve surrounding the bath for the primary cryogen and the bath for the secondary cryogen in the first chamber portion, said sleeve being open at the top and capable of being reversibly lowered from an upper position to a lower position. Accordingly, the sleeve is in its lowered position when the sample is plunged into the secondary cryogen. In a preferred variant, the sleeve is disposed between an outer shell of the first cryopreparation chamber portion and the cooling baths for the primary and secondary cryogens.

For the above reasons, a preferred sub-variant provides that the sleeve of the first chamber portion is in its upper position when the second chamber portion is not placed thereon, and that when the second chamber portion is placed thereon, the sleeve is in its lowered position.

The protective region of cold gas, which is necessary for the transfer of the frozen sample from the cooling bath into the EM specimen holder inserted through the access port, is provided by the second chamber portion.

In order to allow easy positioning of the sleeve by the user, the sleeve may be spring-mounted. The spring-mounted sleeve is pressed by the closed second chamber portion into the lower position against the force of the spring. In order to reliably retain the sleeve in this position, the second chamber portion may be locked to the first chamber portion, for example, via a bayonet connection. It is also advantageous that the sleeve have substantially the shape of a cylindrical tube.

The present invention is, in particular, intended for use in conjunction with an automated cryopreparation device, such as one of the devices described above (Vitrobot, Cryoplunge). Of course, it can also be used to manually cryofix a sample located on a sample support and subsequently transfer the sample support into an EM specimen holder that has been inserted through an access port.

BRIEF DESCRIPTION OF THE DRAWING VIEWS

The present invention and further advantages thereof will now be explained in more detail with reference to a non-limiting exemplary embodiment illustrated in the drawings, in which.

DETAILED DESCRIPTION OF THE INVENTION

Figure 1:
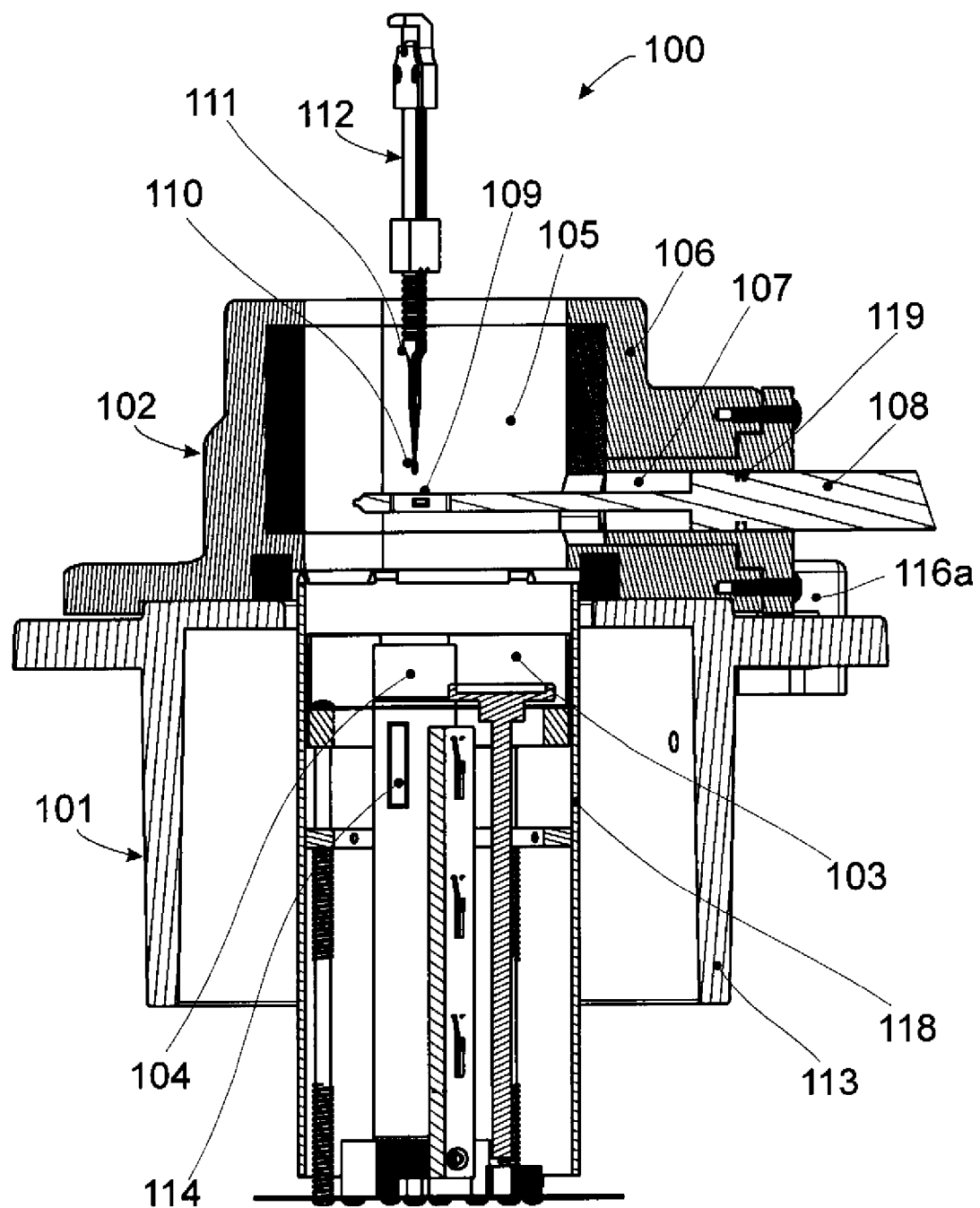
FIG. 1 is a longitudinal section through a cryopreparation chamber according to the present invention.
Figure 2:
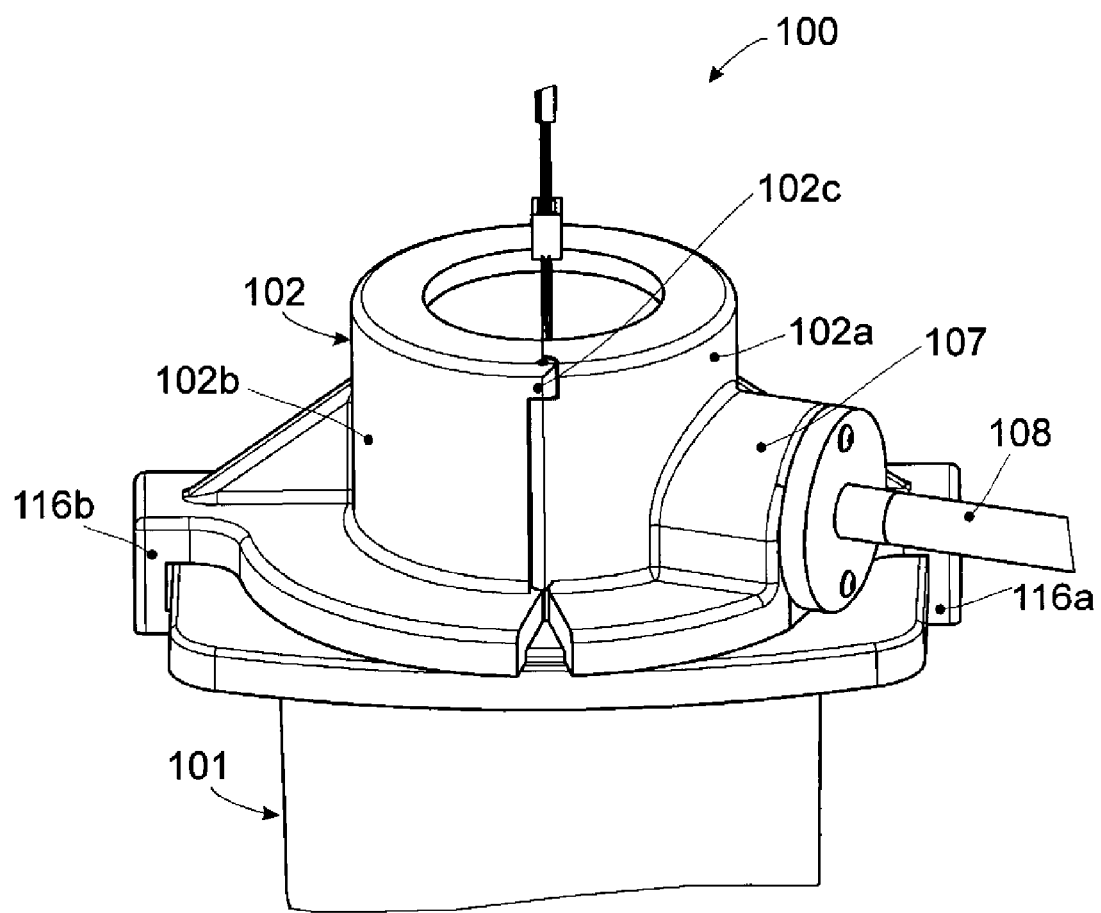
FIG. 2 is a perspective view of the cryopreparation chamber of FIG. 1.
Figure 3:
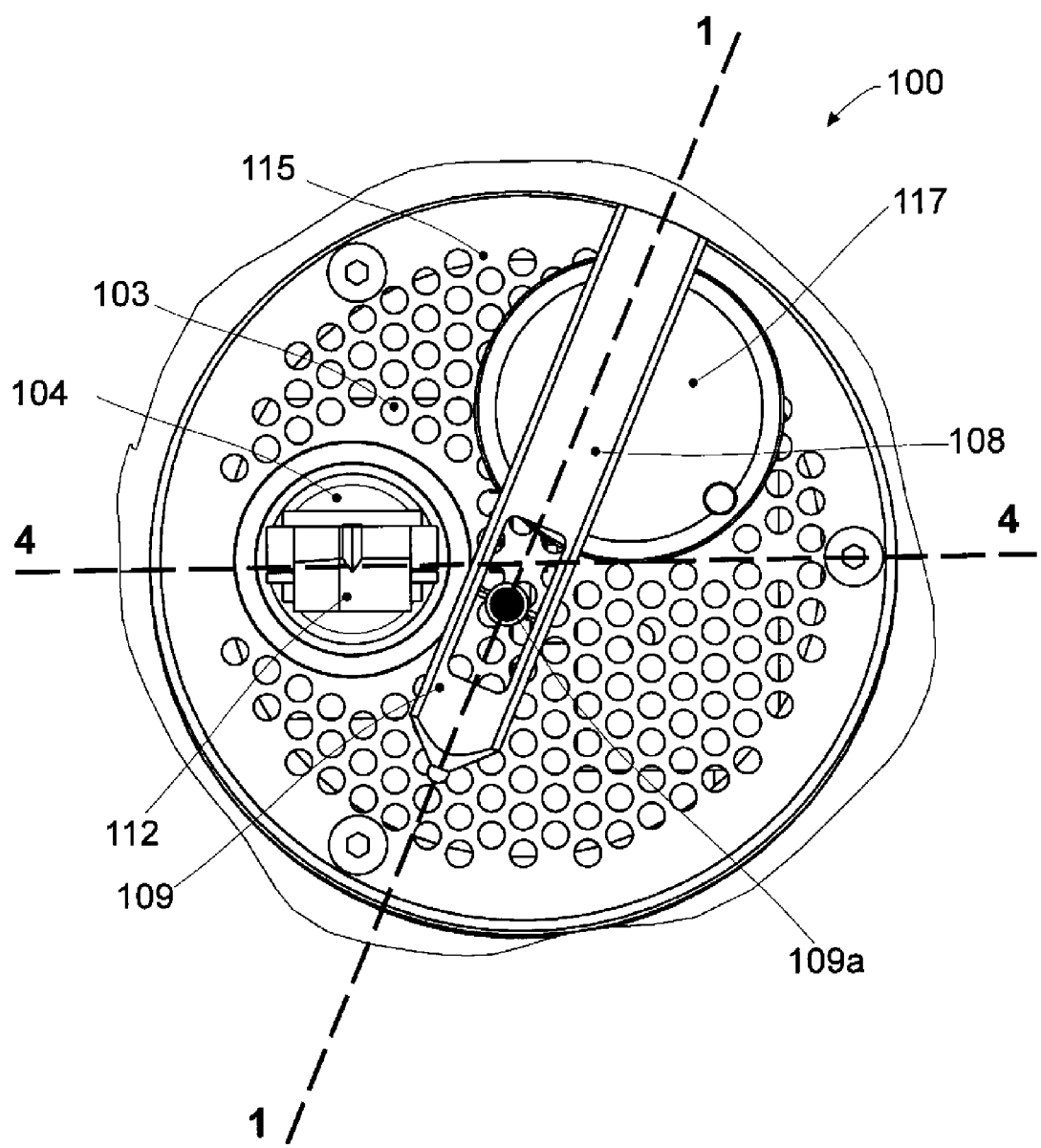
FIG. 3 is a top view of the cryopreparation chamber of FIG. 1.

FIG. 1 shows a longitudinal cross-sectional view of a cryopreparation chamber 100 according to the present invention, taken along line 1-1 of FIG. 3. Cryopreparation chamber 100 is composed of a lower first chamber portion 101 and an upper second chamber portion 102, second chamber portion 102 being placed on first chamber portion 101 and held in position via a bayonet connection by means of positioning elements 116a,116b (in this regard, see also FIG. 2). Cryopreparation chamber 100 is open at the top. Second chamber portion 102 is detachable and removable from first chamber portion 101.

First chamber 101 has provided therein a cooling bath 103 for liquid nitrogen (nitrogen cooling bath 103) and a cooling bath 104 for ethane (ethane cooling bath 104). Ethane cooling bath 104 is disposed in cooling bath 103 for the liquid nitrogen, as a result of which the ethane is cooled by the liquid nitrogen. In addition, evaporation of the liquid nitrogen produces a stream of cold dry gas which flows continuously upward, cooling interior 105 of cryopreparation chamber 100 and keeping it substantially free of ice precipitates. This protective interior 105 filled with cold dry gas can be optimally used for manipulating and transferring the sample. In order to bring the ethane to a desired temperature, ethane cooling bath 104 is warmed by a heater 114. The ethane is brought to a temperature at which it is in the liquid state and which is preferably −170° C.

Second chamber portion 102 is laterally provided, in its outer wall 106, with an access port 107 through which the cooled forward-end portion 109 of a lancet-shaped specimen holder 108 for a transmission electron microscope can be inserted into the interior of the cryopreparation chamber. Specimen holder 108 is sealed against access port 107 in a known manner by an O-ring 119. When specimen holder 108 is not inserted, access port 107 is closed, for example, by a stopper. The specimen holder 108 shown in FIG. 1 is a side-entry goniometer for a cryo-electron microscope. In order to transfer an electron microscopic sample support (grid) from ethane cooling bath 104 into forward-end portion 109 of specimen holder 108, forward-end portion 109 is positioned at the shortest possible distance from ethane cooling bath 104. In FIG. 1, sample support 110 (grid 110) carrying the cryofixed sample is being removed from ethane cooling bath 104 and placed into forward-end portion 109 of cooled specimen holder 108. Grid 110 carrying the cryofixed sample is held by a forceps 111 of a holding device 112.

FIG. 2 shows cryopreparation chamber 100 of FIG. 1 in a perspective view. It can clearly be seen that second chamber portion 102 has substantially the shape of a tube that is divided into two components 102a and 102b. The two components 102a and 102b are pivotably connected to each other by a hinge 102c. Hinge 102c allows second chamber portion 102 to be opened, placed sideways on first chamber portion 101, and be closed again. Access port 107 and specimen holder 108 inserted therethrough are disposed in component 102a. The division of second chamber portion 102 is necessary in order for holding device 112 and grid 110 fixed therein to be enclosed sideways.

FIG. 3 shows cryopreparation chamber 100 of FIG. 1 in a top view. Cooled forward-end portion 109 of specimen holder 108 inserted through access port 107 is positioned above and close to ethane cooling bath 104. Grid 110 is inserted into cutout 109a. Ethane cooling bath 104 extends into cooling bath 103 for the liquid nitrogen, which is located below screen 115. The evaporating cold dry nitrogen gas flows upwardly through screen 115 and cools interior 105 (see also FIG. 1). Screen 115 serves as a trap to prevent the sample or other objects from entering nitrogen cooling bath 103. Holding device 112 is also shown from above. Screen 115 has disposed thereon a cooled platform 117 which may be used to support a transfer box if the grid is intended to be transferred into an EM specimen holder using the conventional transfer method.

Referring back to FIG. 1, cooling baths 103, 104 of first chamber portion 101 are surrounded by a sleeve 118 which, in the example shown, has the shape of a cylindrical tube. Sleeve 118 is disposed between cooling baths 103, 104 and outer shell 113 of first chamber portion 101. Sleeve 118 is spring-mounted and can be lowered from an upper position to a lower position. In FIG. 1, sleeve 118 is in its lower position.

Figure 4:
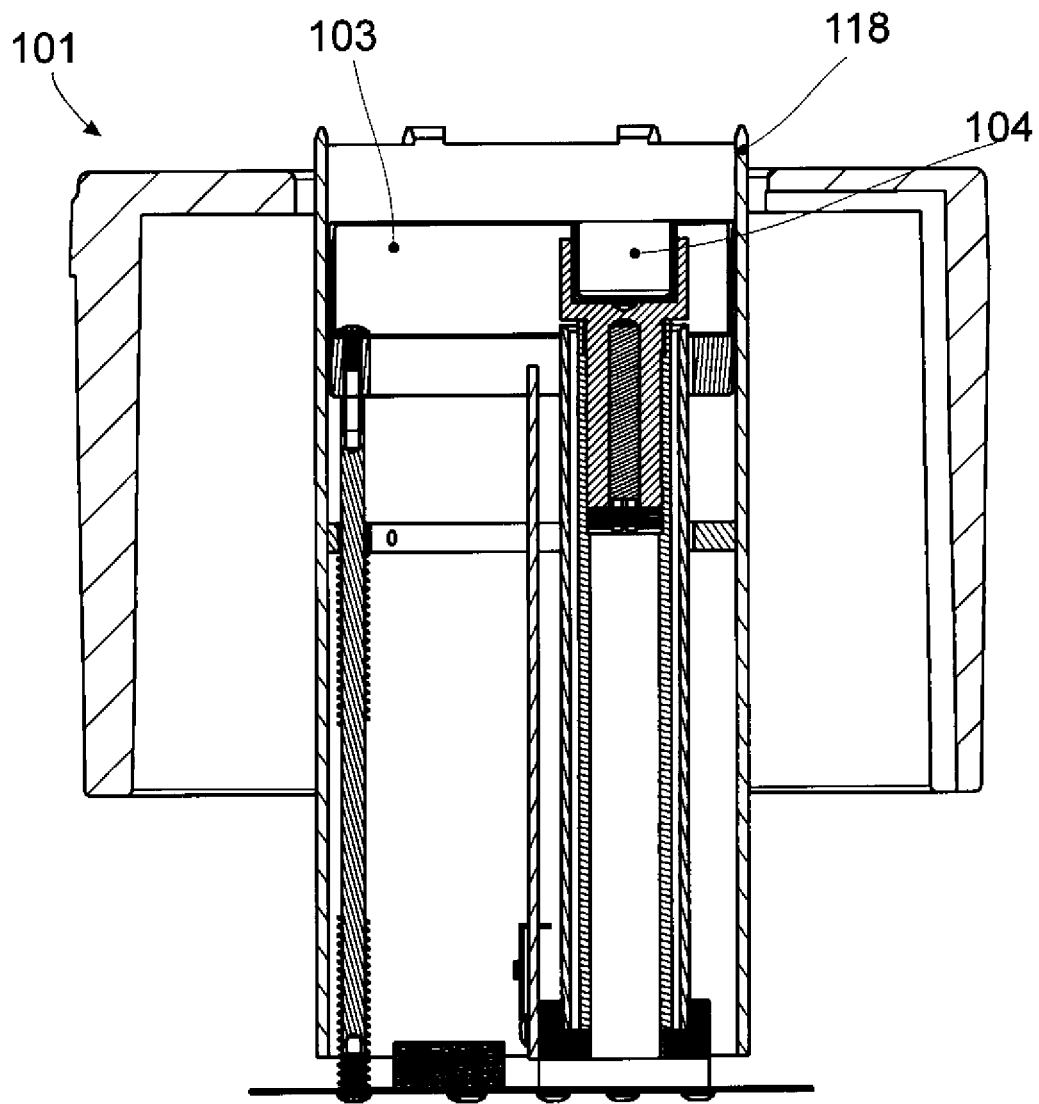
FIG. 4 is a longitudinal section through the first chamber portion of the cryopreparation chamber, showing a spring-mounted sleeve in its lowered position.
Figure 5:
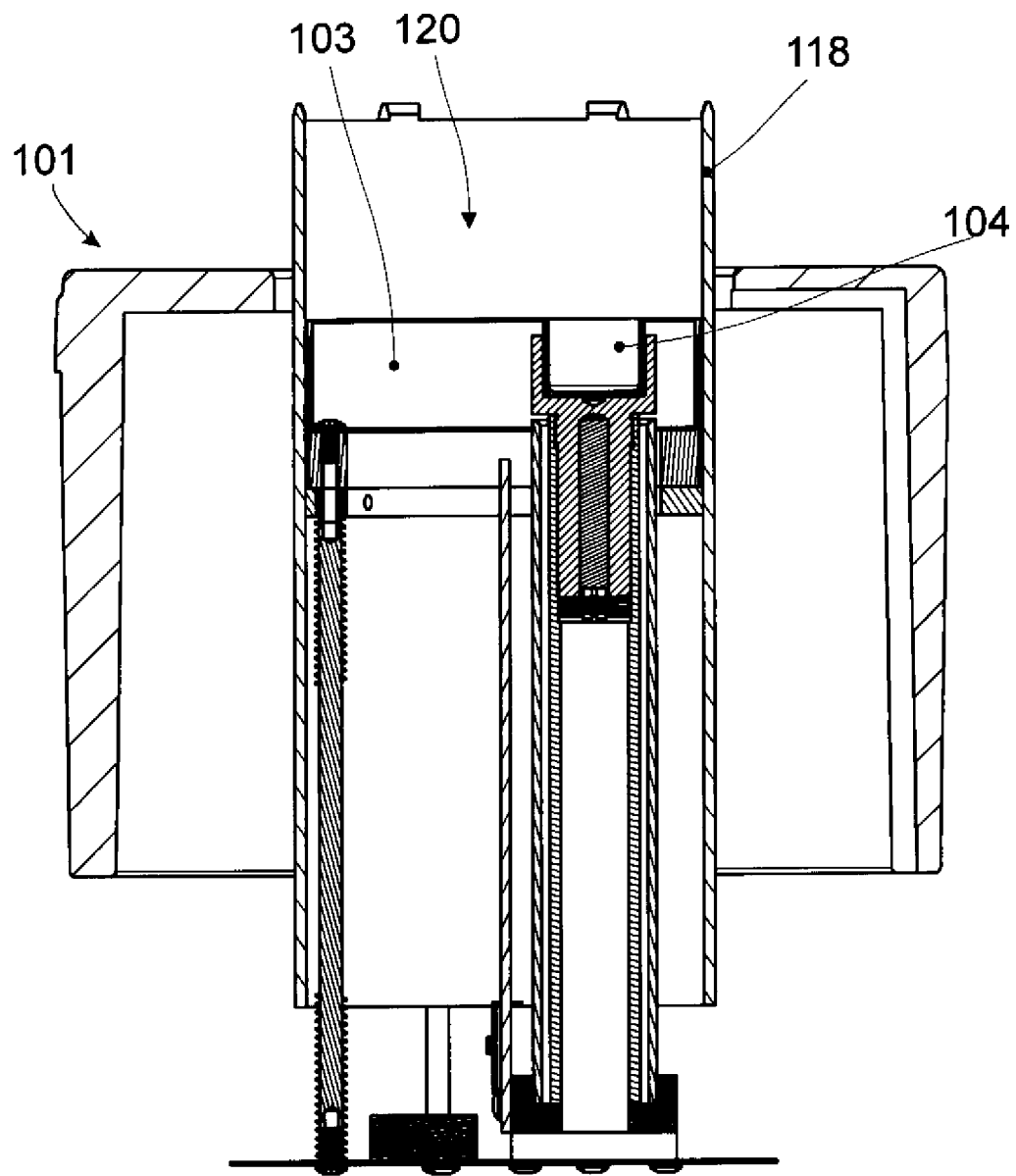
FIG. 5 is another longitudinal section similar to FIG. 4, but showing the spring-mounted sleeve in its upper position.

The typical positions of sleeve 118 are shown in greater detail in FIG. 4 and FIG. 5, which show only first chamber portion 101. FIG. 4 is a longitudinal section through first chamber portion 101, showing sleeve 118 in its lowered position. In FIG. 5, sleeve 118 is in its upper position. Section line 4-4, along which the longitudinal cross-sectional views of FIG. 4 and FIG. 5 are taken, is plotted in FIG. 3 (sectional view only through first chamber portion 101). As can clearly be seen in FIG. 5, sleeve 118 forms a higher cooling region 120 above ethane cooling bath 104, said higher cooling region being cooled by the cold nitrogen evaporating from nitrogen cooling bath 103. This cooling region 120 protects ethane cooling bath 104 from temperature fluctuations and contamination by ambient air, and especially from ice precipitates, when second chamber portion 102 is not placed on first chamber portion 101.

The advantage of a sleeve 118 that can be reversibly lowered will be described in more detail below.

Figure 6:
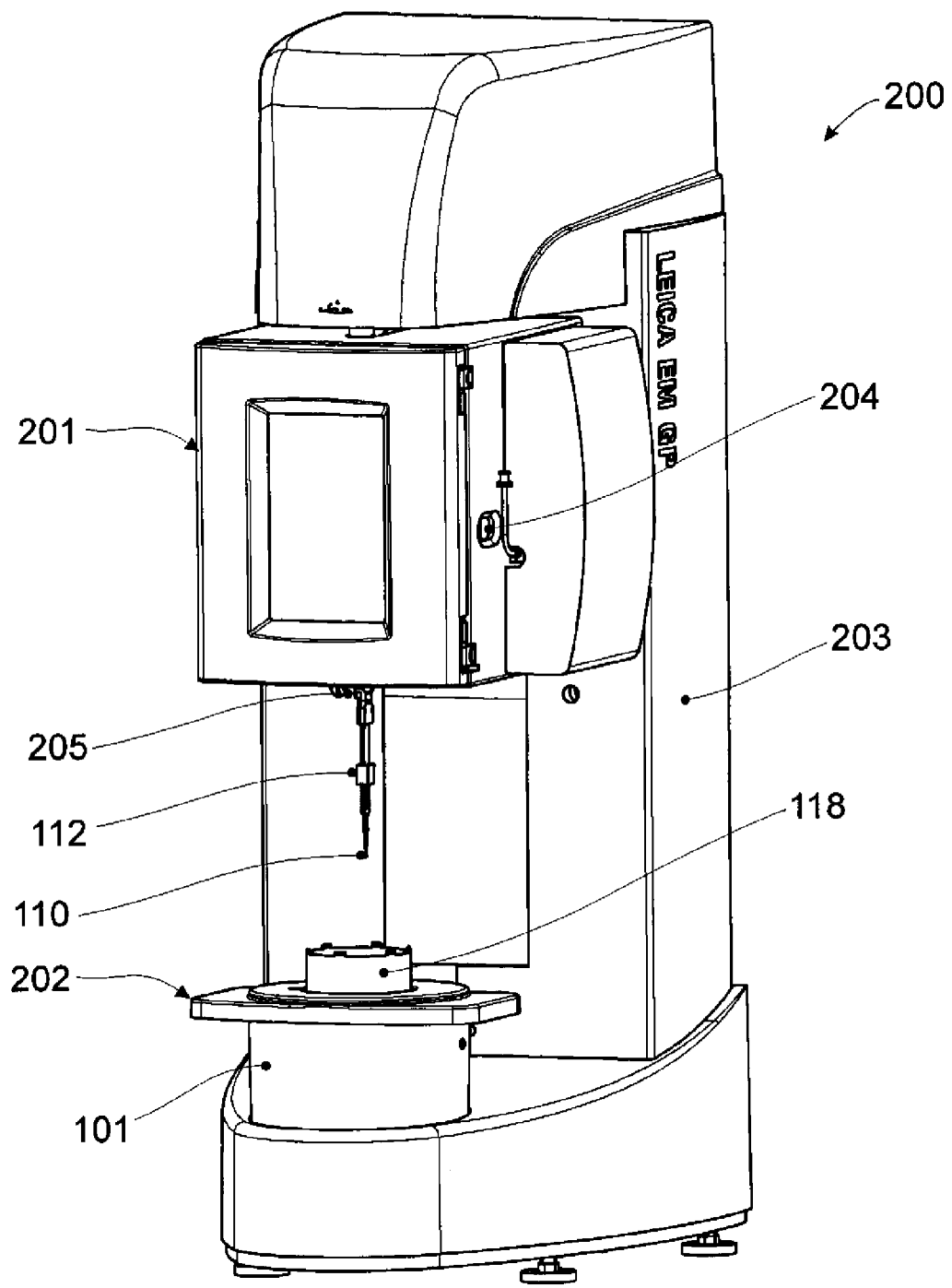
FIG. 6 is a perspective view showing an automated cryopreparation device with the first chamber portion of a cryopreparation chamber according to the present invention.

Cryopreparation of electron microscopic samples may also be carried out manually, but is preferably performed using an automated cryopreparation device because of the better reproducibility. FIG. 6 shows a perspective view of such an automated cryopreparation device 200 for preparing samples for an electron microscope. Device 200 includes as essential components a climate-controlled chamber 201 and a cooling device 202 including the cryopreparation chamber. Enclosed rear portion 203 of device 200 accommodates various stepper motors and a controller, which are not part of the present invention and will not be discussed further herein. FIG. 6 shows only first chamber portion 101 of cryopreparation chamber 100 of the present invention, spring-mounted sleeve 118 of first chamber portion 101 being in its upper position (see also FIG. 5). Second chamber portion 102 is not yet mounted. It is only after sample support 110 is plunged vertically into ethane cooling bath 104 (see FIG. 5) that second chamber portion 102 is placed on first chamber portion 101.

In FIG. 6, climate-controlled chamber 201 of cryopreparation device 200 is shown in its initial position. In this initial position, holding device 112 and grid 110 secured therein can be fixed in a snap-fit coupling 205 of cryopreparation device 200 above first chamber portion 101. When in the upper position (see also FIG. 5), sleeve 118 protects ethane cooling bath 104 from contamination by ambient air, as described earlier herein.

After holding device 112 is fixed in snap-fit coupling 205, climate-controlled chamber 201 is moved downward toward first chamber portion 101 by means of a stepper motor, pushing spring-mounted sleeve 118 through climate-controlled chamber 201 into its lower position (see FIG. 4). Holding device 112 carrying grid 110 is now located inside climate-controlled chamber 201 and at a very short distance above ethane cooling bath 104, because sleeve 118 is in its lowered position. The bottom of climate-controlled chamber 201 is provided with a closure flap (not shown), which clears an opening in the chamber bottom only upon plunging of grid 110 into ethane cooling bath 104. If sleeve 118 were in its upper position, negative effects would occur during the plunging of grid 110 into ethane cooling bath 104, because grid 110 would travel a longer distance through the cold gas before contact with the ethane (lower cooling effect, formation of ice crystals). This disadvantage can be minimized by lowering sleeve 118 into its lower position.

In the next step, the sample liquid is applied to grid 110 via a lateral opening 204 in climate-controlled chamber 201, using a pipette, for example. As described earlier, excess sample liquid can be removed from the grid surface by blotting with filter paper. As with the known devices (e.g., Vitrobot), an automated blotting mechanism is provided in climate-controlled chamber 201 for this purpose. After blotting, the closure flap clears the opening in the bottom of climate-controlled chamber 201, and grid 110 is plunged very rapidly downward into ethane cooling bath 104 of first chamber portion 101 by vertically moving holding device 112, thereby vitrifying the sample located on grid 110. While climate-controlled chamber 201 is moved back upwardly, holding device 112 carrying grid 110 remains in its position.

Next, the vitrified sample located on grid 110 is transferred into specimen holder 108. Referring back to FIG. 1 and FIG. 2 showing cryopreparation chamber 100 of the present invention, second chamber portion 102 is then closed sideways around holding device 112 slightly above first chamber portion 101, in which process second chamber portion 102 is opened and closed, and is then vertically placed on first chamber portion 101 and locked thereto by positioning elements 116a, 116b (bayonet connection). As can be seen in FIG. 1, sleeve 118 remains in its lower position here as well to allow use of access port 107 of second chamber portion 102. After closure and placement of the dividable second chamber portion 102, the cold dry nitrogen gas rises rapidly to the top of second chamber portion 102, cooling interior 105 of the assembled cryopreparation chamber and preventing contamination by ambient air. Protective interior 105 can then be optimally used to manipulate and transfer grid 110 into specimen holder 108.

In the further course of the process, access port 107 is opened and specimen holder 108 is inserted therethrough. Cooled forward-end portion 109 of the specimen holder 108 is brought into close proximity with ethane cooling bath 104. Holding device 112 is manually detached from cryopreparation device 200, and grid 110 is raised out of the ethane. Then, grid 110 is inserted into cutout 109a of forward-end portion 109 of specimen holder 108 (see FIG. 3) and mounted therein. Finally, specimen holder 108 is removed through the access port and inserted into an electron microscope for electron microscopic observation. In order to prevent the frozen sample from melting, such specimen holders typically have a kind of shield which is slid over the grid. To enable microscopic observation, the shield is retracted after the grid is inserted into the cooled cryo-electron microscope.

In a variant not shown, cryopreparation chamber 100 may be portable and removable from cryopreparation device 200. Accordingly, after grid 110 is plunged into the ethane and holding device 112 is detached, the entire cryopreparation chamber 100 may be placed near the electron microscope, and the transfer of grid 110 from the ethane into specimen holder 108 may be carried out locally.

In view of the many possible implementations of the invention, it should be recognized that the implementation described above is only an example of the invention and should not be taken as a limitation on its scope.

LIST OF REFERENCE NUMERALS 100 cryopreparation chamber
101 first chamber portion
102 second chamber portion
103 nitrogen cooling bath
104 ethane cooling bath
105 interior
106 outer wall of the second chamber portion
107 access port
108 specimen holder
109 forward-end portion of the specimen holder
109a cutout for the grid
110 grid
111 forceps
112 holding device
113 outer shell of the first chamber portion
114 heater (not yet sketched in the drawing)
115 grid
116 positioning element
117 platform
118 sleeve
120 higher cooling region
200 cryopreparation device
201 climate-controlled chamber
202 cooling device
203 enclosed rear portion
204 opening in the climate-controlled chamber
205 snap-fit coupling

What is claimed is:

1. A cryopreparation chamber (100) for preparing and manipulating a sample for electron microscopy, the cryopreparation chamber (100) being cooled by a first cryogen, wherein the cryopreparation chamber (100) comprises:
a first chamber portion (101); and
a second chamber portion (102) configured to be detachably placeable on the first chamber portion (101) during cryopreparation of the sample in the first chamber portion, the second chamber portion (102) including an outer wall (106) having an access port (107) through which a specimen holder (108) for an electron microscope can be inserted from a point external to the cryopreparation chamber (100) into the cryopreparation chamber (100).

2. The cryopreparation chamber as recited in claim 1, wherein the second chamber portion (102) includes at least two components (102a,102b) which are reversibly placeable on the first chamber portion (101) in a sideways direction, the access port (107) being provided in one (102a) of the at least two components.

3. The cryopreparation chamber as recited in claim 2, wherein the at least two components (102a,102b) are pivotably connected to each other.

4. The cryopreparation chamber as recited in claim 2, wherein the second chamber portion (102) includes exactly two components (102a,102b).

5. The cryopreparation chamber as recited in claim 1, wherein the second chamber portion (102) has substantially the shape of a cylindrical tube.

6. The cryopreparation chamber as recited in claim 1, wherein the access port (107) of the second chamber portion (102) is adapted for insertion of a side-entry goniometer into the cryopreparation chamber.

7. The cryopreparation chamber as recited in claim 1, wherein the first chamber portion (101) includes a cooling bath (103) for the first cryogen.

8. The cryopreparation chamber as recited in claim 7, wherein the first chamber portion (101) further includes a cooling bath (104) for a second cryogen for freezing electron microscopic samples.

9. The cryopreparation chamber as recited in claim 8, wherein at least a lower portion of the cooling bath (104) for the second cryogen is disposed in the cooling bath (103) for the first cryogen.

10. The cryopreparation chamber as recited in claim 9, further comprising a sleeve (118) surrounding the cooling bath (103) for the first cryogen and the cooling bath (104) for the second cryogen, said sleeve (118) being open at a top thereof and capable of being reversibly lowered from an upper position to a lower position.

11. The cryopreparation chamber as recited in claim 10, wherein the sleeve (118) is in its upper position when the second chamber portion (102) is not placed thereon, and when the second chamber portion (102) is placed thereon, the sleeve (118) is in its lowered position.

12. The cryopreparation chamber as recited in claim 11, wherein the sleeve (118) has substantially the shape of a cylindrical tube.

13. The cryopreparation chamber as recited in claim 10, wherein the sleeve (118) is spring-mounted.

14. A cryopreparation device (200) for cryopreparing a sample for an electron microscope, the cryopreparation device comprising a cryopreparation chamber (100) cooled by a first cryogen, wherein the cryopreparation chamber (100) comprises:
a first chamber portion (101);
a second chamber portion (102) configured to be detachably placeable on the first chamber portion (101) during cryopreparation of the sample in the first chamber portion, the second chamber portion (102) including an outer wall (106) having an access port (107) through which a specimen holder (108) for an electron microscope can be inserted from a point external to the cryopreparation chamber (100) into the cryopreparation chamber (100).

15. The cryopreparation device as recited in claim 14, wherein the first chamber portion (101) includes a cooling bath (103) for the first cryogen and a cooling bath (104) for a second cryogen for freezing electron microscopic samples.

16. The cryopreparation device as recited in claim 15, wherein at least a lower portion of the cooling bath (104) for the second cryogen is disposed in the cooling bath (103) for the first cryogen.

17. The cryopreparation device as recited in claim 16, further comprising a sleeve (118) surrounding the cooling bath (103) for the first cryogen and the cooling bath (104) for the second cryogen, said sleeve (118) being open at a top thereof and capable of being reversibly lowered from an upper position to a lower position.

18. The cryopreparation device as recited in claim 17, wherein the sleeve (118) is in its upper position when the second chamber portion (102) is not placed thereon, and when the second chamber portion (102) is placed thereon, the sleeve (118) is in its lowered position.

19. The cryopreparation device as recited in claim 18, wherein the sleeve (118) has substantially the shape of a cylindrical tube.

20. The cryopreparation device as recited in claim 17, wherein the sleeve (118) is spring-mounted.

\* \* \* \* \*